US010026202B2

(12) United States Patent
Tian et al.

(10) Patent No.: US 10,026,202 B2
(45) Date of Patent: Jul. 17, 2018

(54) WEARABLE MOLECULAR IMAGING NAVIGATION SYSTEM

(71) Applicant: INSTITUTE OF AUTOMATION, CHINESE ACADEMY OF SCIENCES, Haidian District, Beijing (CN)

(72) Inventors: Jie Tian, Beijing (CN); Kunshan He, Beijing (CN); Chongwei Chi, Beijing (CN); Xin Yang, Beijing (CN)

(73) Assignee: INSTITUTE OF AUTOMATION, CHINESE ACADEMY OF SCIENCES, Haidian District, Beijing (CN)

( * ) Notice: Subject to any disclaimer, the term of this patent is extended or adjusted under 35 U.S.C. 154(b) by 0 days.

(21) Appl. No.: 15/289,535

(22) Filed: Oct. 10, 2016

(65) Prior Publication Data

US 2017/0161921 A1 Jun. 8, 2017

(30) Foreign Application Priority Data

Oct. 9, 2015 (CN) .......................... 2015 1 0649648
Oct. 9, 2015 (CN) ..................... 2015 2 0778829 U

(51) Int. Cl.
*G06T 11/00* (2006.01)
*H04N 5/33* (2006.01)
(Continued)

(52) U.S. Cl.
CPC ............ *G06T 11/003* (2013.01); *G01B 11/00* (2013.01); *H04N 5/2256* (2013.01);
(Continued)

(58) Field of Classification Search
USPC ....................................................... 382/128
See application file for complete search history.

(56) References Cited

U.S. PATENT DOCUMENTS 7,420,675 B2 * 9/2008 Giakos ................... B82Y 20/00
356/364
7,899,217 B2 * 3/2011 Uludag .............. G06K 9/00046
340/5.53
(Continued)

FOREIGN PATENT DOCUMENTS

CN 101238974 A 8/2008
CN 101770141 A 7/2010
(Continued)

OTHER PUBLICATIONS

Chinese Office Action for corresponding Chinese Patent Application No. 201510649648.6 dated Sep. 1, 2017, 15 Pages, with English translation.

*Primary Examiner* — Ishrat I Sherali
(74) *Attorney, Agent, or Firm* — Merchant & Gould P.C.

(57) ABSTRACT

The invention discloses a wearable molecular imaging navigation system comprising: a multi-spectral light transceiver configured to transmit a multi-spectral light to a detected subject in a detection region and acquire an emitting light regarding the detected subject and acquire a reflecting light regarding the detected subject; an image processor configured to receive the reflecting light and the emitting light from the multi-spectral light transceiver, execute a three-dimensional reconstruction and fusion process on the reflecting light and the emitting light to obtain a fusion image; a wireless signal processor configured to enable a wireless communication; and a wearable device, configured to receive the fusion image from the image processor via the wireless signal processor, display the fusion image and control the multi-spectral light transceiver and the image processor based on instructions received.

6 Claims, 4 Drawing Sheets

(51) Int. Cl.
  *G01B 11/00* (2006.01)
  *H04N 5/225* (2006.01)
  *A61B 5/00* (2006.01)

(52) U.S. Cl.
  CPC ........... *H04N 5/2258* (2013.01); *H04N 5/332* (2013.01); *A61B 5/0075* (2013.01); *A61B 5/6803* (2013.01)

(56) References Cited

U.S. PATENT DOCUMENTS

| | | | |
|---|---|---|---|
| 2014/0088384 A1* | 3/2014 | Basilion | A61B 18/20 600/317 |
| 2014/0340287 A1* | 11/2014 | Achilefu | A61B 19/56 345/8 |
| 2015/0216398 A1* | 8/2015 | Yang | A61B 1/043 600/109 |

FOREIGN PATENT DOCUMENTS

| | | |
|---|---|---|
| CN | 104083146 A | 10/2014 |
| CN | 104116496 A | 10/2014 |
| CN | 104198458 A | 12/2014 |
| CN | 104305957 A | 1/2015 |
| CN | 204318916 U | 5/2015 |
| CN | 104771139 A | 7/2015 |
| CN | 205094589 U | 3/2016 |
| WO | 2015/168579 A1 | 11/2015 |

* cited by examiner

WEARABLE MOLECULAR IMAGING NAVIGATION SYSTEM

This application claims benefit of Serial No. 201510649648.6, filed 9 Oct. 2015 in China and Serial No. 201520778829.4, filed 9 Oct. 2015 in China and which applications are incorporated herein by reference. A claim of priority is made to each of the above disclosed applications.

TECHNICAL FIELD

The present invention relates to an imaging system, more particularly, to a wearable molecular imaging navigation system.

BACKGROUND

Recently, molecular imaging based on optical imaging technology, information processing technology, molecular biology, chemistry, computational mathematics and the like has become one of hotspots in the imaging field.

SUMMARY

In view of the above, the invention provides a wearable molecular imaging navigation system, which may enhance the accuracy for positioning and facilitate operations of the wearable imaging navigation system by its new-designed structure and a new technology.

The present invention provides a wearable molecular imaging navigation system, comprising:

a multi-spectral light transceiver, configured to transmit a multi-spectral light to a detected subject in a detection region and acquire an emitting light regarding the detected subject and a reflecting light regarding the detected subject;

an image processor, configured to receive the reflecting light and the emitting light from the multi-spectral light transceiver, execute a three-dimensional reconstruction and fusion process on the reflecting light and the emitting light to obtain a fusion image;

a wireless signal processor, configured to enable a wireless communication; and a wearable device, configured to receive the fusion image from the image processor via the wireless signal processor, display the fusion image and control the multi-spectral light transceiver and the image processor based on instructions received.

DETAILED DESCRIPTION

The invention will now be described, by way of example only, with reference to the accompanying drawings.

According to an embodiment of the invention, a wearable molecular imaging navigation system based on excitation fluorescence imaging is provided.

Figure 1:
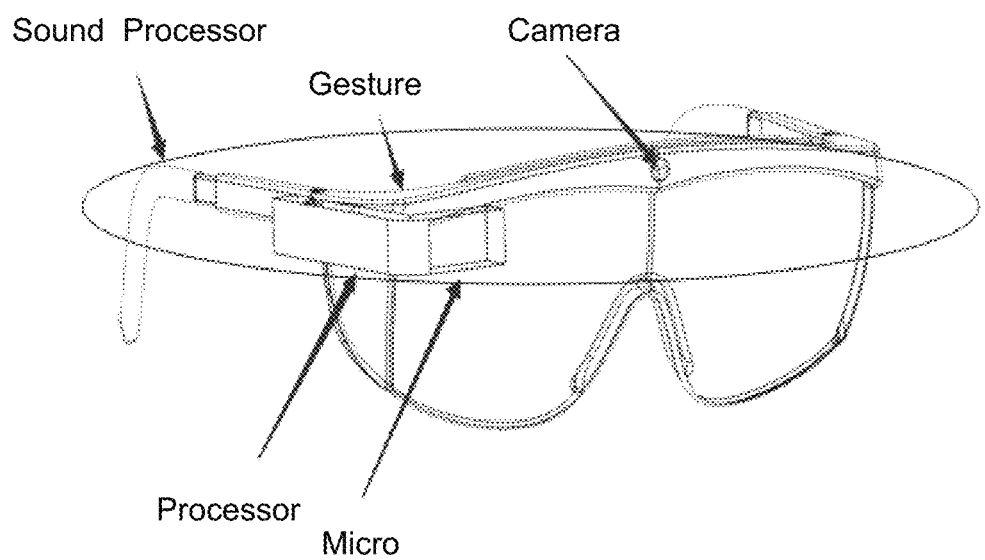
FIG. 1 is a schematic diagram illustrating a wearable device according to an embodiment of the present invention.
Figure 2:
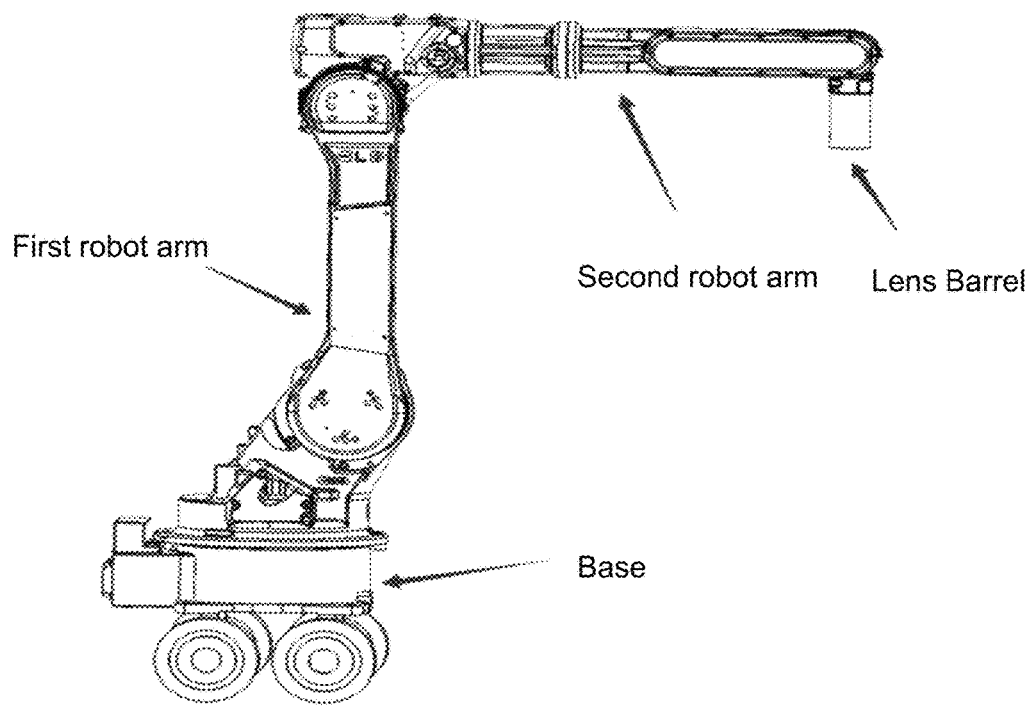
FIG. 2 is a schematic diagram illustrating an integrated structure of a multi-spectral light transceiver, an image processor, and a wireless signal processor according to the embodiment of the present invention.
Figure 3:
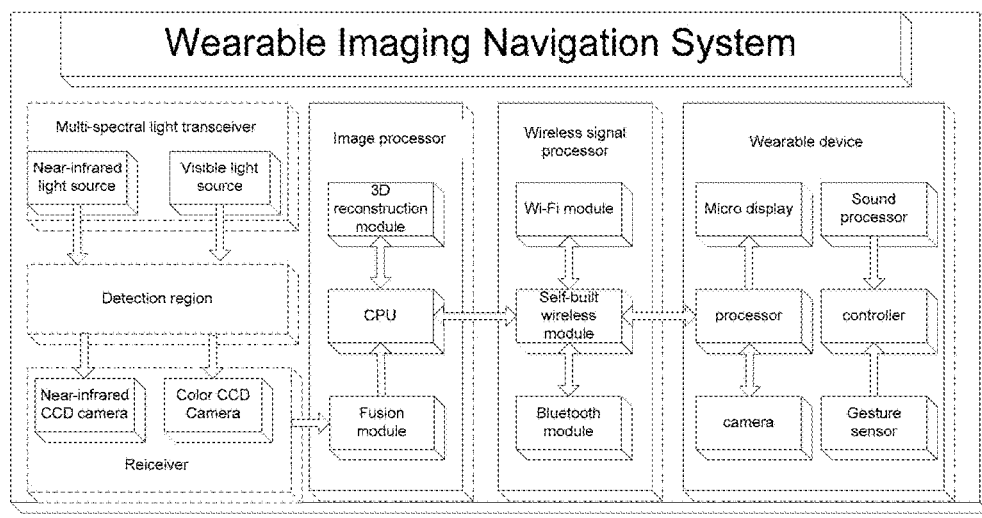
FIG. 3 is a block diagram illustrating a wearable molecular imaging navigation system according to the embodiment of the present invention.

FIG. 1 is a schematic diagram illustrating a wearable device according to the embodiment of the present invention. FIG. 2 is a schematic diagram illustrating an integrated structure of a multi-spectral light transceiver, an image processor, and a wireless signal processor according to the embodiment of the present invention. FIG. 3 is a block diagram illustrating a wearable imaging navigation system according to the embodiment of the present invention. As shown in FIG. 3, the wearable imaging navigation system may comprise:

a multi-spectral light transceiver, configured to transmit a multi-spectral light to a detected subject in a detection region and acquire an emitting light and a reflecting light regarding the detected subject, wherein the emitting light is a near-infrared fluorescence signal and the reflecting light is a visible light signal;

an image processor, configured to receive the reflecting light and the emitting light from the multi-spectral light transceiver, execute a three-dimensional reconstruction and fusion process on the reflecting light and the emitting light to obtain a fusion image;

a wireless signal processor, configured to enable a wireless communication;

a wearable device, configured to receive the fusion image from the image processor via the wireless signal processor, display the fusion image and control the multi-spectral light transceiver and the image processor based on instructions received.

As shown in FIG. 2, the wearable molecular imaging navigation system is mounted on a mechanically integrated structure. The structure may comprise: a base, on which a first robot arm is movably mounted, wherein a second robot arm is movably mounted on the other end of the first robot arm, and a lens barrel is mounted at the front end of the second robot arm.

In the following, the operations of the multi-spectral light transceiver, the image processor, the wireless signal processor and the wearable device will be described in detail.

The multi-spectral light transceiver may mainly comprise:

a visible light source, which may be implemented with a LED cold light source and may be located on the base, so as to emit a visible light to the detected subject in the detection region. Alternatively, a bandpass filter may be disposed before the visible light source, so as to transmit a visible light with a predetermined wavelength. Preferably, the predetermined wavelength is 380 to 700 nm;

a near-infrared laser, which may be disposed above the visible light source and also integrated in the base, so as to emit a near-infrared light to the detected subject. Optionally, the emitted light has a central wavelength of a near-infrared light such as 800 nm;

an optical coupler, which is disposed in the first robot arm and configured to couple the visible light and the near-infrared light and transmit the coupled light to the detected subject through the lens in the lens barrel;

a dichroic splitter, which is disposed on the lens in the lens barrel and configured to split the coupled light reflected by the detected subject into the reflecting light and the emitting light, and deliver the reflecting light and the emitting light to a near-infrared CCD camera and a color CCD camera, respectively; and the near-infrared CCD camera and the color CCD camera, which may disposed on the opposite sides of the front end of the second robot arm (which is the end near the lens barrel), wherein the near-infrared CCD camera is configured to collect a near-infrared light split by dichroic splitter, and the color CCD camera is configured to collect the visible light split by dichroic splitter.

Figure 4:
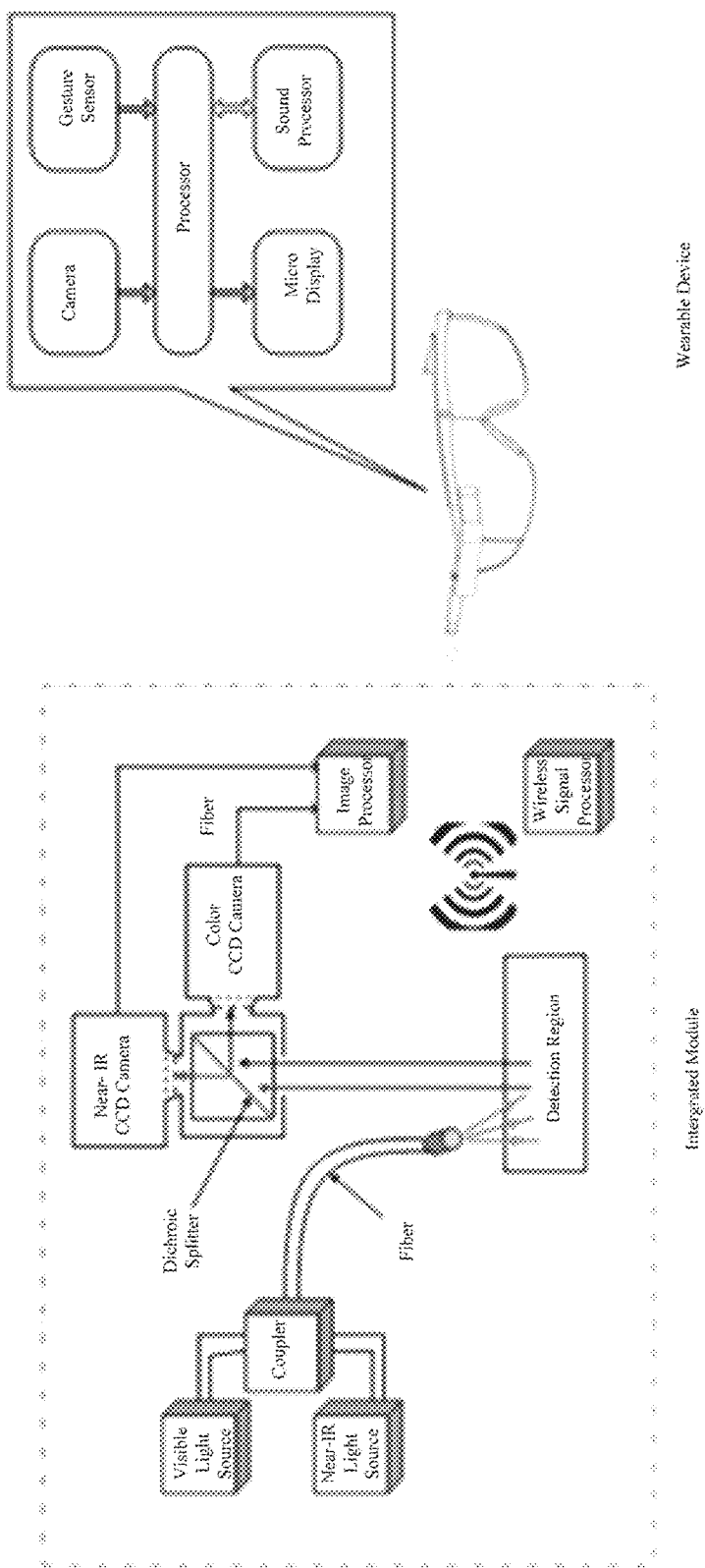
FIG. 4 is a schematic diagram illustrating the wearable molecular imaging navigation system according to the embodiment of the present invention.

The laser emitted by the near-infrared laser can be drawn by an optical fiber. As shown in FIG. 4, the light emitted by the visible light source and the laser light emitted by the near-infrared laser are respectively transmitted to the optical coupler by using optical fibers. The coupled light from the optical coupler is then delivered into the lens in the lens barrel by using an optical fiber, and finally directed to the detection area.

It is known to those skilled in the art that other methods for emitting the visible light and the near-infrared light which are known in the art may be also employed in embodiments of the present invention.

When the coupled light is directed to the detection region, simultaneously outputting of the visible light signal and the near-infrared light signal can be realized by using a single fiber. In particular, the visible light signal and the near-infrared light signal can be coupled by the optical coupler at an outputting port.

The dichroic splitter may be a 750 nm splitter for splitting the coupled light into the emitting light and the reflecting light and for delivering the emitting light and the reflecting light to the near infrared CCD camera and the color CCD camera respectively. The multi-spectral transceiver may also comprise other optical fibers for connecting with the near infrared CCD camera and the color CCD camera respectively, so as to transfer signals to the image processor. After being split by the dichroic splitter, the coupled light is split into the emitting light and the reflecting light. As shown in FIG. 4, the emitting light and reflecting light are directly transmitted to the near-infrared CCD camera and the color CCD camera respectively. Then, the signals obtained by the near-infrared CCD camera and the color CCD camera are delivered into the image processor through a fiber, respectively.

As shown in FIG. 2, the image processor is located at the middle of the second robot arm. As shown in FIG. 4, the signals collected by the near-infrared CCD camera and the color CCD camera are transferred to the image processor through the optical fiber. The image processor may have a CPU itself, in which image processing software can be included. Thus, the collected signal can be processed by the image processor. The image processor can be connected to the wireless processor, and the wireless module can be further connected to the wearable device. Accordingly, the whole system is interconnected. Since the wireless processor and the image processor are only small integrated circuit boards, both of them can be located in the middle of the second robot arm.

The image processor may comprise a processor for obtaining an image corresponding to the reflecting light based on the collected visible light signal, obtaining an image corresponding to the emitting light based on the near-infrared light signal, and then performing the three-dimensional reconstruction and fusion process on the images.

The image processor may preprocess images corresponding to the reflecting light and the emitting light to obtain a more accurate image distribution features. In particular, the preprocessing may include:

for a pixel matrix of the image corresponding to the reflecting light, selecting a sub-matrix window having a predetermined size and being centered on each target pixel, bubble sorting pixel values within the sub-matrix window, and setting a smaller one of two median values as a new pixel value of a target pixel, wherein the predetermined size is preferably 3×4; and for the image corresponding to the emitting light, filtering the image by using a Chebyshev type band-pass filter with a pass band having a first predetermined value, wherein the first predetermined value is the near-infrared wave band in a range of $3.33 \times 10^{14} \sim 3.8 \times 10^{14}$.

The purpose of the preprocessing is to reduce the noise and to enhance the image quality. According to the present invention, different preprocessing is used for the images corresponding to the reflecting light and the emitting light, since the emitting light with a wavelength of $3.33 \times 10^{14} \sim 3.8 \times 10^{14}$ is weak, but it is a desired light for the present invention. Therefore, the emitting light is intercepted, rather than being impaired. While the reflecting light is treated as a background light, the preprocessing for the reflecting light may have a good performance on noise reduction at the expense of a great impairment.

Of course, other preprocesses known in the art may also be performed on the images corresponding to the reflecting light and the emitting light.

Then, the image processor may perform a wavelet multi-resolution decomposition on the preprocessed images respectively to obtain a low frequency information and a high frequency information of the preprocessed images, and perform the fusion process on the low frequency information and the high frequency information respectively, so as to acquire the fused multi-resolution decomposition information; and obtain the fusion image by using a synthesis algorithm.

Preferably, wavelet coefficients are selected according to as follows in the wavelet multi-resolution decomposition:

$$\omega_{i,j} = \begin{cases} \omega_{i,j}^1 & \text{abs}(\omega_{i,j}^1) \geq \text{abs}(\omega_{i,j}^2) \\ a\omega_{i,j}^2 & \text{other} \end{cases}$$

wherein $\omega_{i,j}$ is a horizontal, vertical or diagonal wavelet coefficient of the fusion image at each dimension, $\omega_{i,j}^1$, $\omega_{i,j}^2$ indicate the wavelet coefficients for the images corresponding to the reflecting light and the emitting light, respectively; a is a proportionality coefficient, and $1 \leq a \leq 1.05$.

The image processor may be further configured to perform a three-dimensional point cloud concatenation and fusion process on the reflecting light and the emitting light, so as to acquire a three-dimensional geometric information of the detected subject and restore the three-dimensional geometric information and the color information of surfaces of the detected subject. The three-dimensional point cloud concatenation enables to perform a three-dimensional point cloud concatenation on the signal collected by the wearable device before performing a fusion process. The image processor may further fuse the collected image information directly so as to generate a 2D fusion image, or perform a three dimensional concatenation and fusion on the collected image information by using a three-dimensional point cloud concatenation. With such a three-dimensional fusion, a 3D image which may have a stereoscopic information (i.e. 3D information) and a color information can be obtained after the fusion. While matching features, the image processor may select a subset composed of n data points and perform a RANSAC operation to the subset m times wherein $3 \leq n \leq 9$, $m \geq 200$.

A CPU is used for controlling the above operations, so as to achieve the above functions. In addition, the CPU may also process the image information obtained by any of the wearable devices or the reconstructed three-dimensional image information, according to the instructions from the wearable device, and to transmit the processed information to a micro display.

As shown in FIG. 3, the wireless signal processor may include a Wi-Fi module, a self-built wireless signal module and a Bluetooth module. The Self-built wireless signal module can establish a small wireless network for connecting with other devices without a wireless router, so as to improve the robustness and confidentiality of the system. The wireless signal processor may also connect to other devices through the Bluetooth module or the Wi-Fi module. The wireless signal processor can connect to a plurality of devices at the same time.

As shown in FIG. 3, the wearable device mainly includes a micro display, a processor, a camera, a sound processor, a gesture sensor and the like. The wearable device has a half-rimmed glasses structure with an adjustable slot. Such structure may promote an easy replacing of lens. The camera is suspended before the half-rimmed glasses structure. The processor is provided at a right side of frames and is connected to the micro display. The micro display is configured to replay a received fusion image at a certain distance in front of one eye. The sound processor can enable a communication between wearers and a control of the wearable imaging navigation system by using a bone conduction technology. The gesture sensor can process sensed signals, so as to control the system. The processor can control a content and display manner of the micro display according to different instructions. The half-rimmed glasses structure is a structure of a half of (not all of) the edges of the glasses being surrounded by the frames. If all of the edges of the glasses is surrounded by the frames, the glass has a full-frame structure. In the present invention, the half-rimmed glasses structure is used. As shown in FIG. 1, lens is positioned below the circle, which can facilitate an easy replacing of the lens and an increasing of the view, and can also protect the eyes more carefully, so as to protect the eyes from the laser. Motion sensors and gyroscopes are positioned on different locations of the frames, so as to perceive changes of the head. Each of the above modules is connected to the processor for various functions.

FIG. 4 shows a schematic diagram of the system according to the embodiment of the present invention. As shown in FIG. 4, the above-mentioned preprocessing is performed on the images corresponding to the reflecting light and the emitting light received by the image processor. Then, the geometrical characteristics of the images can be obtained by using a multi-scale geometric analysis. Subsequently, by calculating a variance coherency measure (VHW), determining a local adaptive window to estimate a threshold shrinkage factor of the optimal Contourlet coefficients, and shrinking the Contourlet coefficients, a noise reduction can be further achieved. The noise reduction process can be selectively performed according to the requirement for image quality. If the requirement for image quality is high, such method can be performed to further reduce the noise. If the requirement for image quality is not high, only a pre-process for noise reduction is performed on the images corresponding to the emitting light and the reflecting light. For the noise-reduced images, a improved SIFT algorithm can be used to extract features, so as to get better image feature points and to improve the image fusion quality. Preferably, graphite heat sinks can be attached to the two CCD cameras respectively, which can greatly improve the image quality.

According to the embodiments of the present application, at least one of following advantages may be achieved:
1. An accurate and real-time imaging navigation can be realized by the design of a wearable structure, which also facilitates a user-friendly design;
2. The operator's hands are liberated by the design of a wireless voice control and a head attitude sensing, so as to further facilitate the operations of the wearable molecular imaging navigation system and enhance an interaction with human;
3. By using a multi-angle switching and three-dimensional reconstruction technology, the operator may obtain a better perspective, more information, thereby enhancing the interaction between peoples. Furthermore, it can provide other peoples with a first site of the information; and
4. By improving known algorithms in fields of noise reduction, registration and fusion, a ratio of a detecting signal to a background signal has been improved. Therefore, a better imaging result can be obtained and the navigation becomes more accurate.

While the invention has been described in detail and with reference to specific embodiments thereof, it is to be understood that the above description is intended only as illustrative and not restrictive, which is not intended to limit the scope of the invention. Various modifications, substitutions, improvements and the like within the spirit and principles of the present invention are intended to be included within the scope of the present invention.

We claim:
1. A wearable molecular imaging navigation system, comprising:
   a multi-spectral light transceiver configured to transmit a multi-spectral light to a detected subject in a detection region and acquire a transmitting light regarding the detected subject and acquire a reflecting light regarding the detected subject;
   an image processor configured to receive the reflecting light and the transmitting light from the multi-spectral light transceiver, execute a three-dimensional reconstruction and fusion process on the reflecting light and the transmitting light to obtain a fusion image;
   a wireless signal processor configured to enable wireless communication; and
   a wearable device, configured to receive the fusion image from the image processor via the wireless signal processor, display the fusion image and control the multi-spectral light transceiver and the image processor based on instructions received;
   wherein the image processor is further configured to preprocess images corresponding to the reflecting light and the transmitting light to obtain preprocessed images, prior to executing the three-dimensional reconstruction and fusion process, by:
   for a pixel matrix of the image corresponding to the reflecting light, selecting a sub-matrix window having a predetermined size and being centered on a target pixel, bubble sorting pixel values within the sub-matrix window, and setting a smaller one of two median values as a new pixel value of a target pixel; and for the image corresponding to the transmitting light, filtering the image by using a Chebyshev type bandpass filter with a pass band having a first predetermined value;

wherein the image processor is further configured to perform a wavelet multi-resolution decomposition on the preprocessed images respectively to obtain a low frequency information and a high frequency information of the preprocessed images, and perform the fusion process on the low frequency information and the high frequency information respectively, so as to acquire the fused multi-resolution decomposition information; and obtain the fusion image by using a synthesis algorithm;

wherein the image processor is configured to select wavelet coefficients according to as follows in the wavelet multi-resolution decomposition:

$$\omega_{i,j} = \begin{cases} \omega_{i,j}^1 & \text{abs}(\omega_{i,j}^1) \geq \text{abs}(\omega_{i,j}^2) \\ a\omega_{i,j}^2 & \text{other} \end{cases}$$

wherein $\omega_{i,j}$ is a horizontal, vertical or diagonal wavelet coefficient of the fusion image at each dimension, $\omega_{i,j}^1$, $\omega_{i,j}^2$ indicate the wavelet coefficients for the images corresponding to the reflecting light and the transmitting light, respectively; a is a proportionality coefficient, and $1 \leq a \leq 1.05$.

2. The system according to claim 1, wherein the multi-spectral light transceiver further comprises:

a near-infrared laser, configured to emit a near-infrared light;

a visible light source, configured to emit the visible light;

an optical coupler, configured to couple the visible light and the near-infrared light and transmit the coupled light to the detected subject;

a dichroic splitter, configured to split the coupled light reflected by the detected subject into the reflecting light and the transmitting light;

a near-infrared CCD camera, configured to collect the transmitting light and transmit the transmitting light to the image processor; and a color CCD camera, configured to collect the reflecting light and transmit the reflecting light to the image processor.

3. The system according to claim 1, wherein the wireless signal processor further comprises a built-in rechargeable battery and a built-in wireless network chip, wherein the wireless network chip is configured to independently establish a small wireless network for connecting the multi-spectral light transceiver, enable a Bluetooth connection and a Wi-Fi connection.

4. The system according to claim 1, wherein the wearable device further comprises a micro display, a camera, a processor, a sound processor, and a gesture sensor, wherein the micro display is configured to replay a received fusion image at a certain distance in front of one eye; and the wearable imaging device further comprises a micro rechargeable battery, a motion sensor, and a headset.

5. The system according to claim 1, wherein the image processor is further configured to perform a three-dimensional point cloud concatenation and fusion process on the reflecting light and the transmitting light, so as to acquire a three-dimensional geometric information of the detected subject and restore the three-dimensional geometric information and the color information of surfaces of the detected subject; and wherein the image processor is further configured to select a subset composed of n data points and perform a RANSAC operation to the subset m times while matching features, wherein $3 \leq n \leq 9$, $m \geq 200$.

6. The system according to claim 5, wherein the image processor is further configured to process the reflecting light and the transmitting light or the reconstructed three-dimensional image information, according to the instructions from the wearable device.

* * * * *